United States Patent [19]
Takada

[11] Patent Number: 6,071,234
[45] Date of Patent: Jun. 6, 2000

[54] SELF-PROPELLED COLONOSCOPE

[76] Inventor: Masazumi Takada, 622-26, Takatsukashinden, Matsudo-shi, Chiba-ken, Japan

[21] Appl. No.: 09/207,424

[22] Filed: Dec. 8, 1998

[30] Foreign Application Priority Data

Jun. 3, 1998 [JP] Japan .................................. 10-154601

[51] Int. Cl.⁷ .................................................. A61B 1/01
[52] U.S. Cl. ........................... 600/114; 600/101; 600/152
[58] Field of Search ..................................... 600/101, 114, 600/118, 139, 146, 149, 152; 604/95, 96, 172, 271

[56] References Cited

U.S. PATENT DOCUMENTS

| | | | |
|---|---|---|---|
| 4,066,071 | 1/1978 | Nagel | 600/114 |
| 4,176,662 | 12/1979 | Frazer | 600/114 |
| 4,561,427 | 12/1985 | Takada | 600/114 |
| 5,345,925 | 9/1994 | Allred, III et al. | 600/114 |
| 5,562,601 | 10/1996 | Takada | 600/114 |

*Primary Examiner*—John P. Leubecker
*Attorney, Agent, or Firm*—Young & Thompson

[57] ABSTRACT

A self-propelled colonoscope comprises control part and an insertion tube including a distal part, a bending part, and a flexible part. The distal part is equipped with an image pickup element. Two or more endless belts each of which is circular in cross section extend along the surface of the flexible part from a guide hole positioned at a distance of less than 3 cm from the distal end of the flexible part to the control part. The endless belts are driven by a driving mechanism located at the control part. They are guided from the inner surface of the flexible part to the outer surface through the guide hole. The endless belts are held by guide hooks which are arranged on the outer surface of the flexible part. The length of each endless belt is equal to about 105% to 150% of an imaginary endless belt fully tensioned and extending from said control part to a respective guide hole. The colonoscope can be easily, safely and rapidly inserted into the colon without causing pain to a patient.

2 Claims, 5 Drawing Sheets

SELF-PROPELLED COLONOSCOPE

BACKGROUND OF THE INVENTION

1. Field of the Invention

The present invention relates to a self-propelled colonoscope. That is a self-propelled colonoscope which can be easily inserted into the colon and used for observation, photographing, biopsy and surgical operation of the colon without causing pain to a patient.

2. Description of the Related Art

Examination using an endoscope is widely used for observing, photographing a part of the examination, taking specimen from a lesion to ascertain if a tumor is malignant, removing when the tumor is malignant, observing other pathological and physiological conditions and processes and removing foreign body. An endoscope is also useful in the examination of a colon. In the conventional method of examining a colon using an endoscope, the endoscope must be manually inserted into the colon by pushing it with the hands, even though various other techniques can be applied. Therefore, it frequently occurs that a patient strongly complains of abdominal pain and distension because the colon is extended or excessively dilated and insertion of the endoscope into the colon must sometimes be stopped. Furthermore, it is not unusual for the colon to bleed and be accidentally perforated. In particular, these complaints frequently occur in cases of adhesion of the intestine from a previous abdominal operation. Therefore, a highly standardized technic is required for inserting an endoscope into a colon, and particularly for smoothly inserting the endoscope through the sigmoid colon and into the descending colon and ascending colon. Insertion of an endoscope through the splenic flexure, the transverse colon, the hepatic flexure or an adhesion part caused by previous operation is also accompanied with difficulty. Because of these reasons, a colonoscopy is only performed by a few doctors who are versed in the manipulation of a colonoscope. It is also considered that a patient has to endure some pain and discomfort.

As a colonoscope which can be inserted easily, safely and rapidly without causing pain to a patient, the present inventor proposed in Japanese Patent Application Laid-Open No. Heisei 8(1996)-38416 a self-propelled colonoscope which is equipped with endless belts in the area ranging from a position of 3 to 10 cm from a distal end of a flexible part to a control part and can be smoothly inserted into the colon by driving the endless belt by a driving mechanism located at the control part. This self-propelled colonoscope can be inserted easily without giving pain to a patient. However, further improvement in the property for insertion and decrease in the possibility of causing bleeding in the colon and giving pain to a patient has been desired.

SUMMARY OF THE INVENTION

An object of the present invention therefore is to produce a self-propelled colonoscope which can be rapidly, easily and safely inserted into a colon without giving pain to a patient.

As a result of extensive studies by the present inventor to achieve the above-mentioned object, it was discovered that the property for insertion at the initial period of rotation of the endless belts can be further improved when a self-propelled colonoscope which is equipped with endless belts driven by a driving mechanism located at the control part has said endless belts extending from a position of 0 to 3 cm from the distal end of the flexible part to the control part and that the possibility of bleeding and injury of the wall of the colon can further be decreased by increase in the contact area between the endless belts and the wall of the colon at the initial period of rotation of the endless belts when a self-propelled colonoscope having such a structure is used. The present invention was completed on the basis of this discovery.

Thus, the present invention provides;

(1) A self-propelled colonoscope comprising a control part and an insertion section which comprises a distal part, a bending part and a flexible part. The distal part is equipped with an image pickup device or a bundle of optical fibers which provides a return image guide, and a bundle of optical fibers which provides light guides for illumination. The flexible part is equipped with two or more endless belts. In other words, the self-propelled colonoscope of the present invention can be automatically advanced in the colon by driving the endless belts. Each of the endless belts is circular in cross section and extends along the surfaces of the flexible part in an area ranging from a position of 0 to 3 cm from the distal end of the flexible part to the control part. Each endless belt is driven by a driving mechanism located at the control part, and is transferred from the inner surface of the flexible part to the outer surface through a guide hole formed at a position of 0 to 3 cm from the distal end of the flexible part. Each endless belt is held by guide hooks. These guide hooks are attached to the outer surface of the flexible part and have an arc shape which is greater than 180°. The length of an endless belt is equal to about 105% to 150% of what the length would be when the endless belt is fully tensioned and extends from the driving mechanism located at the control part to the guide hole; and (2) A self-propelled colonoscope described in (1), wherein the number of the endless belt is 100 or less.

Other and further objects, features and advantages of the invention will appear more full from the following description.

BRIEF DESCRIPTION OF THE DRAWINGS

The invention will be described with reference to the accompanying drawing, wherein.

Figure 1:
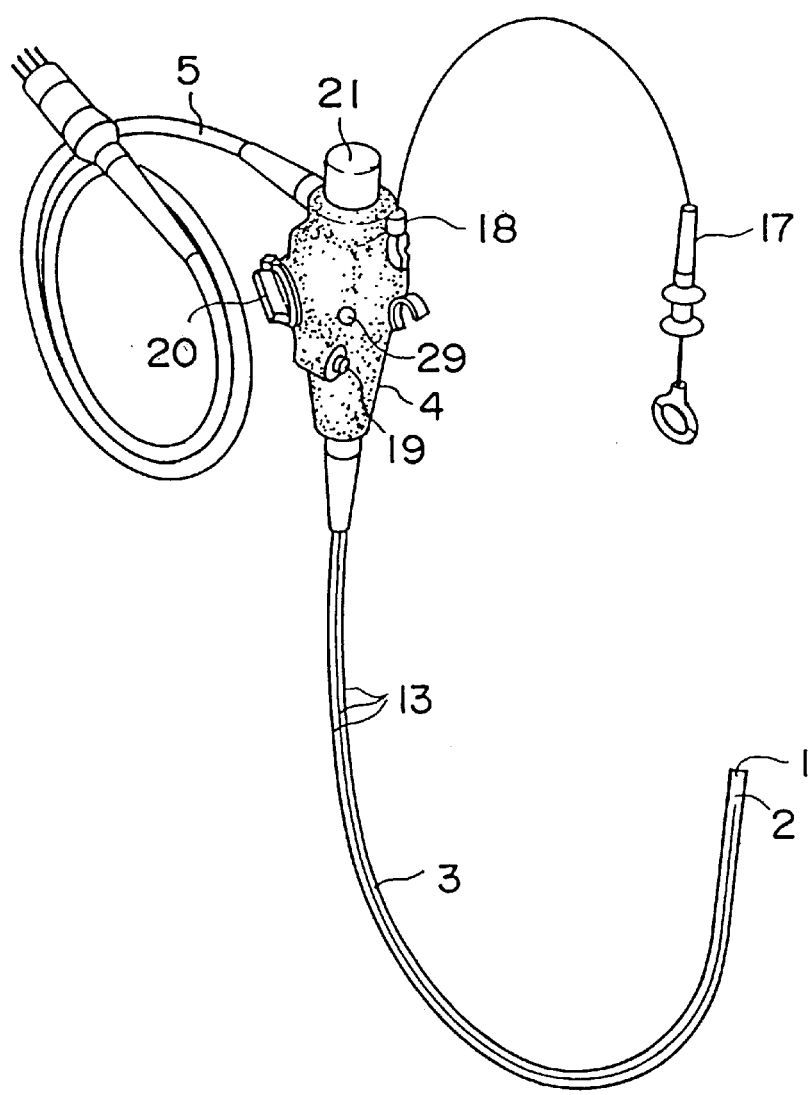
FIG. 1 shows a perspective view of an embodiment of the self-propelled colonoscope of the present invention.

The numbers in the figures have the meanings as listed in the following:

1. a distal part
2. a bending part
3. a flexible part
4. a control part
5. a connection tube 6. a window for receiving an image
7. a window for projecting light
8. an opening for suction and forceps
9. an air/water nozzle
10. an object lens
11. an image pickup device
12. a light guide
13. an endless belt
14. a guide hook
15. a guide pipe
16. a guide hole
17. forceps
18. an opening for insertion of forceps
19. an air/water control valve
20. a control knob
21. a driving mechanism
22. a guide roller
23. a guide roller
24. a row of gears
25. a motor
26. the inside of the flexible part
27. a return image guide
28. an eyepiece section
29. a suction control valve

DETAILED DESCRIPTION OF THE INVENTION

The present invention will now be described in detail with reference to the following drawings.

Figure 2:
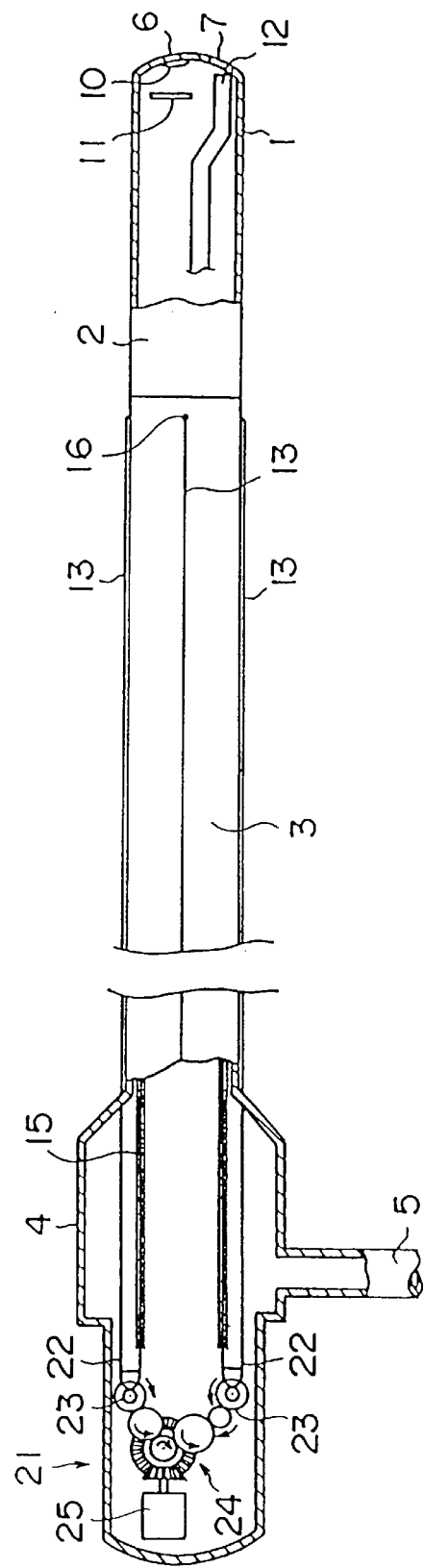
FIG. 2 shows a section view of a part of an embodiment using an electronic scope of the self-propelled colonoscope of the present invention.

FIG. 1 shows a perspective view of an embodiment of the self-propelled colonoscope of the present invention. FIG. 2 shows a section view of a part of an embodiment using an electronic scope of the self-propelled colonoscope of the present invention. The colonoscope of the present invention comprises a distal part 1, a bending part 2, a flexible part 3, and a control part 4 attached to the base end of the flexible part.

Figure 3:
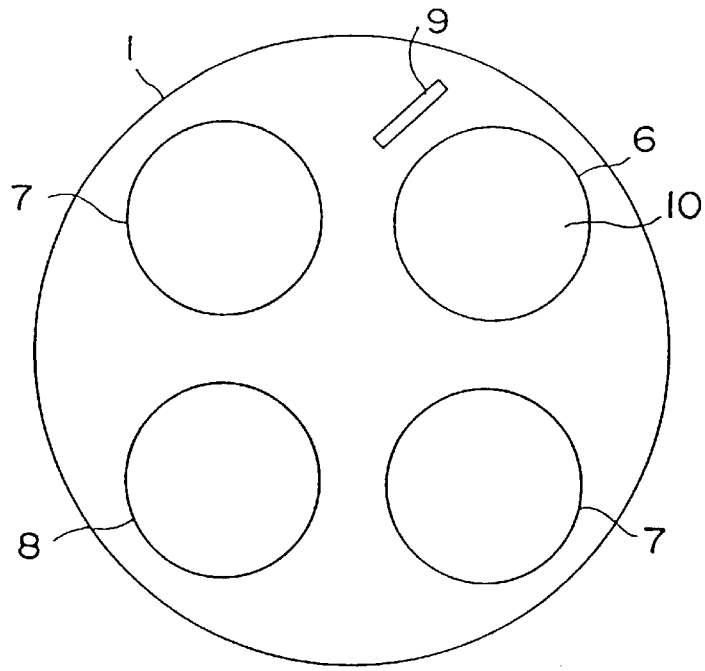
FIG. 3 shows a front view of the distal part.

In the colonoscope of the present invention, the bending part 2 is formed in such a manner that it can be bent in any direction by manipulation of a control knob 20 in the control part 4. FIG. 3 shows a front view of the distal part 1. In the distal part 1, a window 6 fitted with a transparent material receives the image. Two windows 7 fitted with a transparent material project light, and an opening 8 for suction and forceps and an air/water nozzle 9 are also provided in the distal part 1. An object lens 10 and an image pickup device 11 are positioned inside the distal part 1 and face the image receiving window 6. Light guides 12 are also placed inside the distal part 1 at positions facing the light projecting windows 7. As the image pickup device 11, a charge combining device CCD may for example be used.

Figure 4:
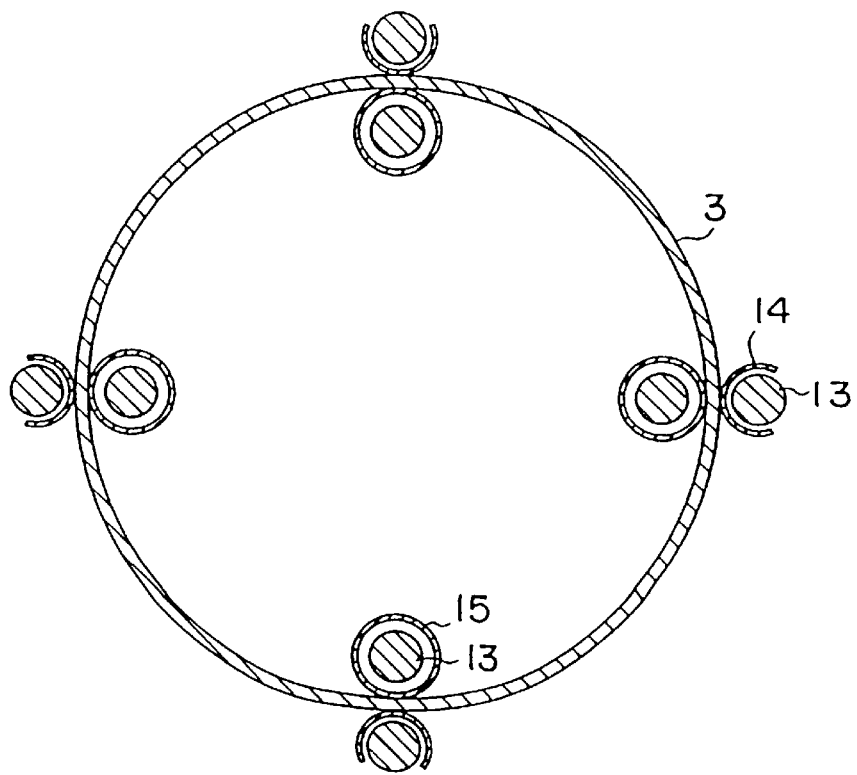
FIG. 4 shows a section view of the flexible part.

FIG. 4 shows a section view of the flexible part 3 of the self-propelled colonoscope of the present invention. The flexible part 3 is equipped with two or more endless belts 13 along surfaces in the longitudinal direction of the colonoscope. When the flexible part 3 is equipped with a single endless belt, the colonoscope is not provided with a smooth self-propelling property. As long as the endless belts 13 are placed along the surface of the flexible part 3 without overlapping with each other, the larger the number of the endless belt, the less the possibility of injuring the surface of mucous membranes of the colon and the better the self-propelling property. The endless belt 13 is held by guide hooks 14 arranged on the outer surface of the flexible part 3. Each guide hook 14 has a diameter slightly larger than the diameter of the endless belt and has an arc shape which is greater than 180°, thereby covering more than one half of the circumferential length of the circle of the cross section of the endless belt. When the guide hook 14 has an arc shape which is equal to or smaller than 180°, thereby covering one half or less of the circumferential length of the circle of the cross section of the endless belt 13, the guide hook 14 cannot hold the endless belt 13. The guide hooks 14 are arranged on the outer surface of the flexible part 3 with a distance ranging from 0 to 90 cm, preferably 0 to 20 cm, more preferably 0 to 6 cm, from each other in the longitudinal direction of the flexible part 3.

Inside of the flexible part 26 of the colonoscope are disposed guide pipes 15 for the endless belts 13, a lead wire for transmitting image signals received at the image pickup device 11 to an outside apparatus, such as a monitoring apparatus or a bundle of optical fibers for the return image guide, a bundle of optical fibers for the light guide, a tube for supplying air and water, a guide tube for suction and forceps, mechanisms used for the operation and other elements as needed. These mechanisms are omitted in FIG. 4.

Figure 5:
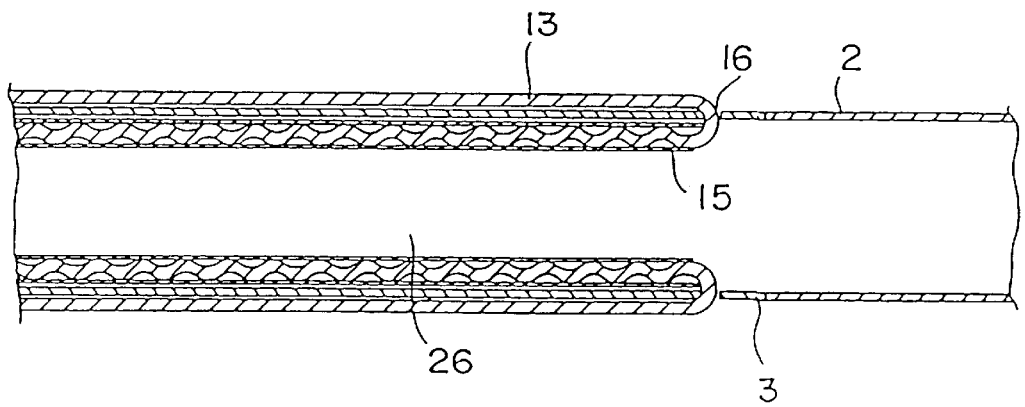
FIG. 5 shows a section view of the part around the distal end of the flexible part.
Figure 6:
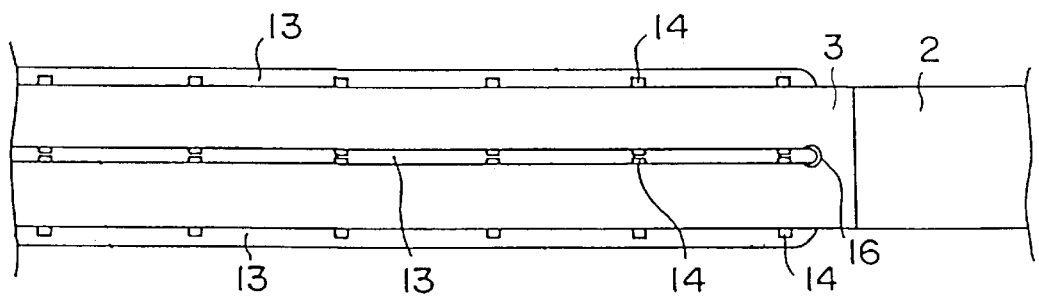
FIG. 6 shows a plane view of the part around the distal end of the flexible part.

FIG. 5 shows a section view of the part around the distal end of the flexible part. FIG. 6 shows a plane view of the part around the distal end of the flexible part. The endless belt which travels within a guide pipe 15 inside of the flexible part toward the distal end of the flexible part is guided to the outside of the flexible part via a guide hole 16 formed at a position ranging from 0 to 3 cm from the distal end of the flexible part. By forming a guide hole at a position ranging from 0 to 3 cm from the distal end of the flexible part, the property for insertion at the initial period of rotation of the endless belt of the self-propelled colonoscope can further be improved because of increase in the contact area between the endless belts and the wall of the colon at the initial period of rotation of the endless belt and the possibility of causing bleeding from the wall of the colon and giving pain to a patient can further be decreased because of increase in the contact area between the endless belt and the wall of the colon at the initial period of rotation of the endless belt. When the distance of the position of the guide hole from the distal end of the flexible part exceeds 3 cm, the property for insertion of the self-propelled colonoscope is inferior and there is the possibility that bleeding from the wall of the colon occurs and pain is given to a patient although there is an advantage in that the flexible part has less possibility of having a damage.

In the colonoscope of the present invention, the endless belt emerges to the outside of the flexible part through the guide hole and is returned toward the control part by a driving mechanism located at the control part. The endless belts disposed on the surface of the flexible part of this particular colonoscope touch the wall of the colon. By the movement of the endless belts, the colonoscope moves toward the inner parts of the colon. It is not necessary to push the colonoscope manually into the colon. The guide hole is preferably made fluid-tight with an O-ring or a bearing to prevent penetration of foreign bodies from the colon into the inside of the flexible part. When an O-ring is used, one made of a material having a small friction resistance, such as polytetrafluoroethylene, is suitable. A bearing made of plastics, such as nylon, or metal, such as stainless steel, can be used when a bearing is used. The guide pipe 15 is required to have a diameter larger than that of the endless belt because the endless belt is relaxed in the guide pipe.

In this colonoscope, the length of the endless belt is equal to 105 to 150% of an imaginary belt fully tensioned and extending from the driving mechanism located at the control part to the guide hole positioned at a distance of 0 to 3 cm from the distal end of the flexible part when the flexible part is kept straight. By providing an endless belt with a length equal to 105 to 150% of a n imaginary fully tension ed endless belt extending between the guide hole and the driving mechanism, the endless belt can effectively follow the bending of the flexible part, even when the flexible part of the colonoscope passes through a bent part like the sigmoid colon. Thus, the colonoscope can be inserted inside the colon with stability. The material of the endless belt is not particularly limited, but carbon fiber is preferable.

In the colonoscope of the present invention, an endless belt having a diameter of 1 to 3 mm and a flexible part having a diameter of 8 to 30 mm are preferably used.

On the outside of the control part 4 of this colonoscope are disposed several elements. These include a flexible connection tube 5 for leading various kinds of wire, the bundle of optical fibers for the light guides 12 and various kinds of tubing passing through the inside of the flexible part 3 to the outside, an opening for insertion of forceps 18, a suction control valve 29, an air/water control valve 19 and a control knob 20 for bending the bending part 2 in any direction. On the inside of the control part 4, there is provided a driving mechanism 21 for driving the endless belt 13. The driving mechanism 21 is comprised of a pair of guide rollers, 22 and 23, holding the endless belt between them and a motor 25 rotating one of the guide rollers 23 through a row of gears 24 comprised of spur wheels and bevel gears.

In using the colonoscope of the present invention the distal part 1 is manually inserted directly from the anus to the upper end of the rectum. Then, the motor 25 is rotated to drive the guide roller 23 which in turn drives the endless belt 13. Since the endless belts 13 are circular in cross section and placed along the outer surface of the flexible part, they are in contact with the wall of the rectum. The flexible part is transferred further within the colon by the friction between the endless belts and the wall of the rectum. Thereafter, the distal part, the bending part and the flexible part pass through the sigmoid colon and are self-propelled to reach the deepest point of the colon by the effect of friction between the walls of the colon and the rectum and the endless belts. The sigmoid colon is pulled back toward the rectum because the endless belts are rotated to advance. Therefore, the end of the descending colon is brought close to the distal end of the colonoscope, and the descending colon and the sigmoid colon are linearly arranged. Thus, the colonoscope can be inserted through the sigmoid colon to the descending colon without causing pain. The transverse colon is pulled back toward the descending colon by the advancement of the endless belts through the transverse colon while the endless belts are rotated. This places the transverse colon and the ascending colon in an arrangement having an abtuse angle between them. Thus, the colonoscope can be inserted into the ascending colon through the transverse colon without giving pain to a patient. In this manner, the distal end of the flexible part is guided along the wall of the colon by the driving of the endless belts, even at the bent portions of the colon. The distal part can be inserted into the desired part in the colon without causing pain to the patient. The distal part can be adjusted to any desired direction using the control knob 20. It is not at all necessary to push the colonoscope manually into the colon.

In the colonoscope of the present invention, the endless belts are equipped along substantially the entire length of the outer surface of the flexible part. The longer the portion of the flexible part inserted into the colon, the larger the area of contact between the endless belts and the wall of the colon. Thus, the distal part can be safely inserted to a desired deep part in the colon without causing excessive friction on particular parts of the wall of the colon. Furthermore, the endless belts are firmly held to the flexible part during bending of the flexible part caused by bending of the colon, and are kept in place along the wall of the colon thanks to the guide hooks. Therefore, injury of the wall of the colon will be prevented and advance of the colonoscope in the colon will not be impaired.

Figure 7:
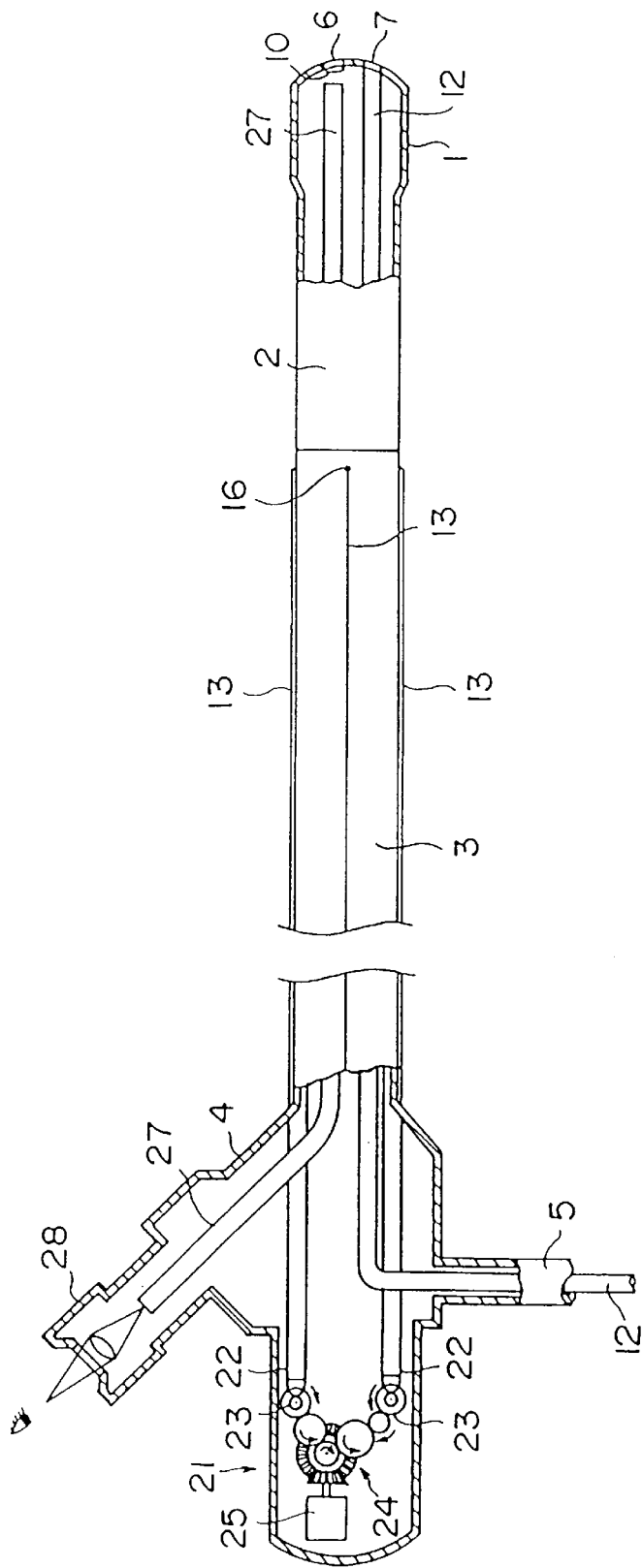
FIG. 7 shows a section view of a part of an embodiment using an fiber scope of the self-propelled colonoscope of the present invention.

The self-propelled colonoscope of the present invention can be used in both electronic scopes and fiber scopes. FIG. 7 shows a section view of a part of an embodiment using an fiber scope of the self-propelled colonoscope of the present invention. In such a colonoscope, the image picked up through the window for receiving an image at the distal part can be directly observed at the eyepiece section 28 through the bundle of optical fibers of the return image guide 27.

To summarize the advantages of the present invention, the self-propelled colonoscope of the present invention can be safely and rapidly inserted into the colon without causing pain to a patient even when the flexible part is bent, because the endless belts are provided along the outer surface of the flexible part in the longitudinal direction and extend from a position of 0 to 3 cm from the distal end of the flexible part to guide rollers, and the colonoscope is guidedly driven by the effect of friction between the endless belts and the wall of the colon, the rectum and the cecum.

While the invention has been depicted and described with reference to preferred embodiments thereof, it will be understood by those skilled in the art that the foregoing and other changes in form and details can be therein without departing from the spirit and scope of the invention.

I claim:

1. A self-propelled colonoscope comprising: a control part, and an insertion section which comprises a distal part, a bending part, and a flexible part having a throughbore and an outer surface comprising a plurality of guide hooks, each guide hook having an arc shape which is greater than 180°, said bending part extending between said flexible part and said distal part, and said flexible part extending between said control part and said bending part, drive means located at said control part for driving at least two endless belts each of which is circular in cross section, each endless belt extending between said control part and a respective guide hole of a plurality of guide holes, each guide hole extending through said flexible part from said outer surface to said throughbore, each guide hole being positioned less than 3 cm from an interface of said bending part and said flexible part, each endless belt extending within said flexible part in said throughbore from said control part to a respective guide hole and then extending external of said flexible part along said outer surface through respective guide hooks of said plurality of guide hooks from a respective guide hole back to said control part, the length of each endless belt being equal to about 105% to 150% of an imaginary endless belt fully tensioned and extending from said control part to a respective guide hole.

2. A self-propelled colonoscope according to claim 1, wherein the number of the endless belts is 100 or less.

* * * * *